United States Patent [19]

Sikkenga et al.

[11] Patent Number: 5,256,817
[45] Date of Patent: Oct. 26, 1993

[54] METHOD FOR PURIFYING A NAPHTHALENEDICARBOXYLIC ACID

[75] Inventors: David L. Sikkenga, Wheaton; Stephen V. Hoover, Aurora, both of Ill.

[73] Assignee: Amoco Corporation, Chicago, Ill.

[21] Appl. No.: 900,618

[22] Filed: Jun. 18, 1992

[51] Int. Cl.$^5$ ............................................ C07C 51/487
[52] U.S. Cl. .................................... 562/487; 562/416; 562/417; 562/488
[58] Field of Search ................ 562/416, 417, 487, 488

[56] References Cited

U.S. PATENT DOCUMENTS

| | | | |
|---|---|---|---|
| 3,584,039 | 6/1971 | Meyer | 562/481 |
| 3,888,921 | 6/1975 | Yamamoto et al. | 562/485 |
| 4,794,195 | 12/1988 | Hayashi et al. | 562/414 |
| 4,933,491 | 6/1990 | Albertins et al. | 562/416 |

OTHER PUBLICATIONS

Xu et al., "Chemistry of Synthetic High Polymers," vol. 10, pp. 107–111, (1984).

Primary Examiner—José G. Dees
Assistant Examiner—Vera C. Clarke
Attorney, Agent, or Firm—Thomas E. Nemo; Wallace L. Oliver; Frank J. Sroka

[57] ABSTRACT

A method for purifying a naphthalenedicarboxylic acid comprising contacting an impure naphthalenedicarboxylic acid with hydrogen in the presence of a hydrogenation catalyst and a solvent comprising a low molecular weight carboxylic acid, at a temperature of at least about 500° F., and a pressure sufficient to maintain the solvent at least partially in the liquid phase and thereafter recovering purified naphthalenedicarboxylic acid.

22 Claims, No Drawings

METHOD FOR PURIFYING A NAPHTHALENEDICARBOXYLIC ACID

FIELD OF THE INVENTION

This invention relates to a method for improving the purity of a naphthalenedicarboxylic acid and particularly 2,6-naphthalenedicarboxylic acid.

BACKGROUND OF THE INVENTION

Naphthalenedicarboxylic acids such as 2,6-, 2,7-, 1,5- and 1,4-naphthalenedicarboxylic acid as well as their corresponding dialkylesters can be used to prepare a variety of polyamide and polyester materials. For example, dimethyl-2,6-naphthalenedicarboxylate and 2,6-naphthalenedicarboxylic acid can be reacted with ethylene glycol to prepare poly(ethylene-2,6-naphthalate) (PEN). Fibers and film manufactured from PEN have improved strength and superior thermal properties relative to other polyester materials. Films made from PEN demonstrate, for example, superior resistance to gas diffusion and particularly to the diffusion of carbon dioxide, oxygen and water vapor. Because of its exceptional properties, PEN is especially suitable for applications such as food and beverage containers, particularly for so-called "hot-fill" food and beverage containers, tire cord, magnetic recording tape and electronic components.

Although the dialkyl-2,6-naphthalenedicarboxylates—particularly dimethyl-2,6-naphthalenedicarboxylate—are suitable monomers for preparing PEN and other polymeric materials, in some commercial-scale operations it is preferable to employ 2,6-naphthalenedicarboxylic acid rather than a dialkyl ester. For example, a polyester manufacturer may have equipment and associated processes available for manufacturing polyesters only from an aromatic dicarboxylic acid. In these circumstances, the diester materials would not be suitable and the use of 2,6-naphthalenedicarboxylic acid would be required. Additionally, it is advantageous to use 2,6-naphthalenedicarboxylic acid in the manufacture of polyesters because the condensation of a diacid with a glycol to form a polyester does not form an alcohol by-product as does the condensation of a diester with a glycol. Polyester manufacturers who use diacids such as 2,6-naphthalenedicarboxylic acid do not, therefore, have to provide for the use or sale of the alcohol by-product.

Methods for preparing naphthalenedicarboxylic acids include the bromine promoted, metal catalyzed, liquid phase oxidation of dialkylnaphthalenes. Such processes are disclosed in U.S. Pat. Nos. 3,870,754; 4,950,786 and 4,933,491. The bromine-promoted, metal-catalyzed, liquid phase oxidation of 2,6-dialkylnaphthalenes, particularly 2,6-dimethylnaphthalene, produces a crude product containing a variety of impurities such as brominated 2,6-naphthalenedicarboxylic acids, 2-formyl-6-naphthoic acid, 2-naphthoic acid and trimellitic acid. These impurities, particularly 2-formyl-6-naphthoic acid, are difficult to remove from crude 2,6-naphthalenedicarboxylic acid. The 2,6-naphthalenedicarboxylic acid must, however, be purified before it can be polymerized to form polymeric materials.

The purification of 2,6-naphthalenedicarboxylic acid is considerably more difficult than the purification of a dialkyl-2,6-naphthalenedicarboxylate primarily due to the low solubility of 2,6-naphthalenedicarboxylic acid in most ordinary solvents, and to its high melting point. In the aforementioned U.S. Pat. No. 4,933,491, for example, 2,6-naphthalenedicarboxylic acid was purified only after reacting the 2,6-naphthalenedicarboxylic acid with a lower alkanoic anhydride to produce a component that is soluble in excess alkanoic anhydride. The "solubilized" 2,6-naphthalenedicarboxylic acid was optionally treated with one or more purification procedures. Xu et al. (Chemistry of Synthetic High Polymers, Vol. 10, pp. 107–11, 1984, Chemical Abstracts CA 102: 185547z) describes the purification of 2,6-naphthalenedicarboxylic acid by routine sublimation, recrystallization or distillation as inefficient and difficult due to the poor solubility of 2,6-naphthalenedicarboxylic acid and also because the impurities present, having similar properties, adhere to each other. U.S. Pat. No. 3,649,680 to McNamey discloses a process for purifying aromatic carboxylic acids wherein a mixture of water and an alkanol are added to an impure carboxylic acid paste, the carboxylic acid is separated from the alkanol/water mixture, and the purified carboxylic acid is subsequently washed with water. U.S. Pat. No. 3,671,578 to Ogata discloses a process for preparing 2,6-naphthalenedicarboxylic acid wherein the monoalkali salt of 2,6-naphthalenedicarboxylic acid is heated in water or a water-containing organic solvent, causing disproportion thereof into 2,6-naphthalenedicarboxylic acid and the dialkali salt of 2,6-naphthalenedicarboxylic acid. U.S. Pat. No. 3,888,921 to Yamamoto et al., discloses a process for purifying 2,6-naphthalenedicarboxylic acid wherein an aqueous solution of a dialkali salt of crude 2,6-naphthalenedicarboxylic acid is prepared, then 40 to 97 mole percent of the dialkali salt is precipitated as a monoalkali salt while maintaining the pH of the aqueous solution at a value of not lower than 6.3, and converting the precipitate to 2,6-naphthalenedicarboxylic acid. It is disclosed in the Yamamoto et al. patent that the aqueous solution of the dialkali salt of 2,6-naphthalenedicarboxylic acid can be at a temperature of 60° C.–350° C. in the presence of potassium or sodium hydroxide, and it is disclosed that the solution can be treated with a reducing agent such as hydrogen gas, sodium dithionite, lithium aluminum hydride or sodium borohydride. U.S. Pat. No. 3,781,346 to Norton discloses a process for purifying naphthalene carboxylic acids comprising reacting a solid ammonium salt of the acid with steam at a temperature of from about 200° C. to about 300° C. U.S. Pat. No. 4,794,195 to Hayashi et al. discloses that as it is impossible to purify crude naphthalenedicarboxylic acid to a high purity only by crystallization, and that it is necessary to combine the method of crystallization with other methods such as thermal treatment, oxidative treatment or reductive treatment. However, no specific means for conducting such treatments on 2,6-naphthalenedicarboxylic or other naphthalenedicarboxylic acid is disclosed. U.S. Pat. No. 3,584,039 to Meyer discloses a process for preparing fiber-grade terephthalic acid by catalytic hydrogen treatment of dissolved impure terephthalic acid.

Methods for purifying a naphthalenedicarboxylic acid, such as those described above, that require an alkanoic anhydride or an alkali metal or ammonium salt to solubilize the naphthalenedicarboxylic acid have their drawbacks in that the anhydride or salt that is formed has to be converted to the free acid. Thus, the art needs an improved method for purifying a naphthalenedicarboxylic acid and the present invention provides such a method.

SUMMARY OF THE INVENTION

A method for purifying a naphthalenedicarboxylic acid comprising contacting the naphthalenedicarboxylic acid with hydrogen in the presence of a hydrogenation catalyst and a solvent comprising a low molecular weight carboxylic acid, at a temperature of at least about 500° F., and at a pressure sufficient to maintain the solvent at least partially in the liquid phase and, thereafter, recovering naphthalenedicarboxylic acid having an improved purity.

The method of this invention not only increases the purity of the naphthalenedicarboxylic acid, but also provides for a naphthalenedicarboxylic acid having a large mean particle size and a very small amount of "fines." The increased particle size and low levels of "fines" improves washing operations, and also provides for improved, low-viscosity slurries with glycols. The slurries are used in the preparation of polyester materials from the naphthalenedicarboxylic acids.

Additionally, the method of this invention converts bromo-naphthalenedicarboxylic acids into naphthalenedicarboxylic acids. Bromo-naphthalenedicarboxylic acids are present in the product when bromine components are used during the liquid phase oxidation of the naphthalene compound to the naphthalenedicarboxylic acid. The method of this invention also greatly reduces the amount of trimellitic acid in the naphthalenedicarboxylic acid and the mother liquor produced after separating the purified naphthalenedicarboxylic acid from the reaction mixture after treatment with hydrogen contains low levels of trimellitic acid. Trimellitic acid, if recycled to an oxidation reaction, will complex to and deactivate oxidation catalyst metals. Consequently, the purification method of this invention allows for the recycle of such mother liquor to the oxidation reaction mixture.

The use of a low molecular weight carboxylic acid as a constituent of the solvent used in the method of this invention permits operation at lower pressures than would otherwise be necessary if only water were used as a solvent and, the low molecular catalyst carboxylic acid facilitates the elimination of oxidation catalyst metals from the naphthalenedicarboxylic acid. Finally, the method of this invention can be used to purify the naphthalenedicarboxylic acid in the dicarboxylic acid form and does not require a mono-alkali, dialkali or other salt, or the anhydride derivative of the naphthalenedicarboxylic acid.

DETAILED DESCRIPTION OF THE INVENTION

The naphthalenedicarboxylic acids that can be purified by the method of this invention include 1,2-, 1,3-, 1,4-, 1,5-, 1,6-, 1,7-, 1,8-, 2,3-, 2,6 and 2,7-naphthalenedicarboxylic acid. The method of this invention is particularly suitable for purifying 2,6-naphthalenedicarboxylic acid. Any known method for preparing these naphthalenedicarboxylic acids can be used; however, the method of this invention is particularly suitable for purifying a naphthalenedicarboxylic acid prepared by the liquid phase, heavy metal catalyzed oxidation of a dialkyl- or alkyl-acylnaphthalene compound. Such dialkyl or alkyl-acylnaphthalene compounds that can be oxidized by a liquid phase, heavy metal catalyzed oxidation reaction include compounds having structure:

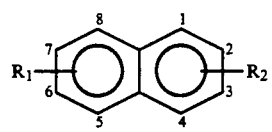

wherein $R_1$ and $R_2$ are independently selected from a hydrocarbyl group having 1 to about 6 carbon atoms, an acyl group having 2 to about 6 carbon atoms or a formyl group. Specific examples of such naphthalene compound include 2,6-dimethylnaphthalene, 2-methyl-6-acetylnaphthalene, 2-methyl-6-butrylnaphthalene, 1,4-dimethylnaphthalene, 2,3-dimethylnaphthalene, 2,6-diethylnaphthalene, 2,6-diisopropylnaphthalene and the like. Sikkenga et al. U.S. Pat. Nos. 5,034,561; 5,030,781 and 4,950,825 disclose methods for preparing dimethylnaphthalene, in Hagen et al. U.S. Pat. No. 5,026,917, a process for preparing 2-methyl-6-acetylnaphthalene is disclosed, and in Hagen et al., U.S. Pat. No. 4,873,386, a process for preparing 2,6-diethylnaphthalene is disclosed.

The most preferred aromatic feed compound for preparing a naphthalene dicarboxylic acid is 2,6-dimethylnaphthalene. Oxidation of 2,6-dimethylnaphthalene produces 2,6-naphthalenedicarboxylic acid which, as described hereinabove, is a suitable monomer for preparing PEN, a high-performance polyester. Furthermore, 2,6-dimethylnaphthalene is superior to, for example, 2,6-diethyl- or 2,6-diisopropylnaphthalene because it is lower in molecular weight and the yield of 2,6-naphthalenedicarboxylic acid per given weight of 2,6-dialkylnaphthalene compound is greater for 2,6-dimethylnaphthalene than for 2,6-diethyl- or 2,6-diisopropylnaphthalene.

Methods for conducting the liquid phase, heavy metal catalyzed oxidation of an alkyl- or acyl-substituted aromatic compound—such as the naphthalene compounds described hereinabove—to the corresponding aromatic carboxylic acid are well known in the art. For example, U.S. Pat. Nos. 4,950,786; 4,933,491; 3,870,754 and 2,833,816 disclose such oxidation methods. In general, suitable heavy metal oxidation catalysts include those metals having an atomic number of about 21 to about 82, inclusive. The preferred oxidation solvent is a low molecular weight monocarboxylic acid having 2 to about 8 carbon atoms, inclusive, preferably it is acetic acid or mixtures of acetic acid and water. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of molecular oxygen is also required, and typically it is air.

A particularly suitable method for oxidizing dialkyl or alkylacylnapthalene compounds, and particularly 2,6-dimethylnaphthalene, to naphthalenedicarboxylic acids is disclosed in U.S. Pat. No. 4,933,491 to Albertins et al. Suitable solvents for such liquid phase oxidation reaction of dialkyl or alkylacylnapthalene compounds include low molecular weight carboxylic acids such as benzoic acid, any aliphatic $C_2$-$C_6$ monocarboxylic acid such as acetic acid, propionic acid, n-butyric acid, isobutyric acid, n-valeric acid, trimethylacetic acid, caproic acid, and water. Preferably the solvent is a mixture of water and acetic acid, which mixture is preferably 1 to 20 weight percent water. The source of molecular oxygen employed in such liquid phase oxidation of the dialkyl or alkylacylnapthalene compounds can vary in molecular oxygen content from that of air to oxygen gas. Because of economy, air is the preferred source of molecular oxygen.

The catalyst employed in such oxidation of the dialkyl or alkylacylnapthalene compounds comprises a bromine-containing compound and at least one of a cobalt- and manganese-containing compound. Preferably, the catalyst comprises cobalt-, manganese-, and bromine-containing components. The ratio of cobalt (calculated as elemental cobalt) in the cobalt component of the catalyst to dialkyl or alkylacylnapthalene compound in the liquid phase oxidation is in the range of about 0.1 to about 100 milligram atoms (mga) per gram mole of dialkyl or alkylacylnaphthalene compound. The ratio of manganese (calculated as elemental manganese) in the manganese component of the catalyst to cobalt (calculated as elemental cobalt) in the cobalt component of the catalyst in the liquid phase oxidation is in the range of from about 0.1 to about 10 mga per mga of cobalt. The ratio of bromine (calculated as elemental bromine) in the bromine component of the catalyst-to-total cobalt and manganese (calculated as elemental cobalt and elemental manganese) in the cobalt and manganese components of the catalyst in the liquid phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine-to-total cobalt and manganese milligram atom ratio is provided by a suitable bromine source such as elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzyl-bromide, tetrabromoethane, ethylenedibromide, etc.). The total bromine in molecular bromine and ionic bromide is used to determine satisfaction of the elemental bromine-to-total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 335° F. to 440° F., has been found to yield about 3 effective gram atoms of bromine per gram mole.

In operation, the minimum pressure at which the oxidation reactor is maintained is that pressure which will maintain a substantial liquid phase of the dialkyl or alkylacylnapthalene compound and at least 70 weight percent of the solvent. The dialkyl or alkylacylnapthalene compound and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range within the oxidation reactor is generally from about 250° F., preferably from about 350° F. to about 450° F., preferably to about 420° F. The solvent residence time in the oxidation reactor is generally from about 20 to about 150 minutes and preferably from about 30 to about 120 minutes.

The oxidation can be performed either in a batch, continuous, or semicontinuous mode. In the batch mode, the dialkyl or alkylacylnapthalene compound, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the dialkyl or alkylacylnapthalene compound has been completely introduced into the reactor, the temperature of the reactor contents is raised. In the continuous mode, each of the dialkyl or alkylacylnapthalene compound, air, solvent, and catalyst are continuously introduced into the reactor, and a product stream comprising naphthalenedicarboxylic acid and catalyst components dissolved in the solvent is withdrawn from the reactor. In the semicontinuous mode, the solvent and catalyst are initially introduced into the reactor and then the dialkyl or alkylacylnapthalene compound and air are continuously introduced into the reactor. For large-scale commercial operation it is preferable to use a continuous oxidation process. In such a process using 2,6-dimethylnapthalene as the feed, the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 370° F. to about 420° F. Acetic acid is the most suitable solvent for such preferred continuous oxidation of 2,6-dimethylnaphthalene.

Subsequent to the oxidation reaction, the oxidation reaction mixture is typically cooled to promote the crystallization of the naphthalenedicarboxylic acid from the reaction mixture; and the naphthalenedicarboxylic acid is partitioned (i.e. separated) from the oxidation reaction mixture by any suitable means for separating a solid from a liquid phase. For example, by centrifugation, filtration and the like. The separated naphthalenedicarboxylic acid is typically washed with one or more solvents either at ambient or, preferably, an elevated temperature. Most suitably the wash solvent is water, acetic acid or other low molecular weight aliphatic carboxylic acid or mixtures of water and a low molecular weight carboxylic acid.

Naphthalenedicarboxylic acids and particularly 2,6-naphthalenedicarboxylic acid produced by the hereinabove described oxidation, typically have impurities such as trimellitic acid, formyl naphthoic acid and, when a bromine compound is used as a promoter, bromo-naphthalenedicarboxylic acid. For example, when the feed to the oxidation reaction is 2,6-dimethylnaphthalene, the resulting 2,6-naphthalenedicarboxylic acid contains up to about 5 wt. % trimellitic acid up to about 1 wt. % 2-formyl-6-naphthoic acid and up to about 3 wt. % bromo-2,6-naphthalenedicarboxylic acids. These impurities must, however, be substantially removed before the naphthalenedicarboxylic acids and particularly the 2,6-naphthalenedicarboxylic acid are used for preparing polyester materials such as PEN.

The method of this invention wherein the impure naphthalenedicarboxylic acid is treated with hydrogen in a liquid phase solvent comprising a low molecular weight carboxylic acid and at a temperature of at least about 500° F. substantially removes these impurities. It is particularly significant that the trimellitic acid is not only removed from the impure naphthalenedicarboxylic acid, but is actually converted to other materials such as, for example, terephthalic acid and isophthalic acid. Therefore, the mother liquor remaining after the purified naphthalenedicarboxylic acid is removed from the reaction solvent can be more readily recycled to an oxidation reaction mixture. Otherwise, the trimellitic acid strongly complexes to and inactivates oxidation catalyst metals. Recycle of the mother liquor obtained from the purification method is desirable because it contains valuable materials such as residual catalyst metals, naphthalenedicarboxylic acids and intermediates that can be oxidized to naphthalenedicarboxylic acids when subjected to oxidation reaction conditions. Additionally, the bromo-naphthalenedicarboxylic acids present, for example, the bromo-2,6-naphthalenedicarboxylic acids, are converted to naphthalenedicarboxylic acids by the method of this invention.

The solvent used for the purification method of this invention comprises a low molecular weight carboxylic acid, preferably containing 1 to about 8 carbon atoms, and preferably a saturated aliphatic low molecular weight monocarboxylic acid containing 2 to about 6 carbon atoms. For example, benzoic acid, acetic acid, propionic acid, n-butyric acid, isobutyric acid, n-valeric acid, trimethylacetic acid, caproic acid and the like. Mixtures of low molecular weight carboxylic acids are also suitable. Acetic acid, because of availability and cost, and also because it is the preferred solvent for the hereinabove described oxidation reaction, is the most preferred solvent. Mixtures of one or more low molecular weight carboxylic acid solvents, particularly acetic acid, and water are also preferred. The amount of water can range from about 1 to about 99 wt. %. Preferably, the amount of water is about 5 to about 95 wt. %. A highly preferred solvent is a mixture of water and acetic acid wherein the water is present in an amount of about 15 wt. % to about 85 wt. %.

The amount of solvent used should be an amount that at least partially, and preferably, substantially completely dissolves the naphthalenedicarboxylic acid at the temperature used for the purification method. For example, preferably at least 50 wt. %, more preferably at least 80 wt. % should be in solution. A suitable weight ratio of solvent to naphthalenedicarboxylic acid is about 2:1 to about 20:1, preferably about 3:1 to about 10:1. Example 3 hereinbelow provides solubility data for 2,6-naphthalenedicarboxylic acid.

The reaction temperature from the purification treatment is at least about 500° F., preferably at least about 550° F. and, more preferably at least about 600° F. At these temperatures, particularly and a temperature of about 600° F. and above, the elimination of trimellitic anhydride from the impure naphthalenedicarboxylic acid is most effective and the rates of the chemical reaction involved in the purification method are greatest. Additionally, solubility of the naphthalenedicarboxylic acid is greater at a high temperature of 600° F. and above and, therefore, lower ratios of the solvent to the naphthalenedicarboxylic acid can be used. An upper limit for the reaction is preferably about 700° F. Above this temperature, unless very short reaction times are used, decomposition of the naphthalenedicarboxylic acid may occur.

In the method of this invention, hydrogen and a suitable hydrogenation catalyst are used. The hydrogen is typically hydrogen gas at a partial pressure (at ambient temperature) of about 1 to about 1000 psig, and preferably about 5 to about 300 psig. The overall reaction pressure should be sufficient to maintain the reaction mixture at least partially in the liquid phase and preferably at least about 50 weight percent of the solvent is in the liquid phase, more preferably at least about 75% weight percent of the solvent is in the liquid phase. Suitably, the overall pressure is about 200 psig to about 3000 psig. An inert gas, such as nitrogen, helium or argon, can be used with the hydrogen gas. An advantage of the present invention wherein a low molecular weight carboxylic acid is used rather than water is the ability to conduct the reaction at lower pressures. For example, at a temperature of 600° F., the vapor pressure of water is 1558 psig, whereas the vapor pressure of a mixture of 85 wt. % acetic acid and 15 wt. % water is only 1050 psig. Thus, by using a low molecular weight carboxylic acid or mixtures thereof with water, lower reaction pressures can be used.

The use of the low molecular weight carboxylic acid also facilitates the removal of the oxidation catalyst metals that would otherwise become entrained with the naphthalenedicarboxylic acid. Additionally, use of a low molecular weight carboxylic acid inhibits the formation of naphthoic acid—formed by the decomposition of a naphthalenedicarboxylic acid—and it also inhibits the formation of dicarboxytetralins—which are formed by the hydrogenation of one aromatic ring of the naphthalenedicarboxylic acid nucleus.

The hydrogenation catalyst required for the method of this invention can be any hydrogenation catalyst that will catalyze the reaction of hydrogen with impurities and provide for the elimination of the formyl naphthoic acid and/or bromo-naphthalenedicarboxylic acids in the impure naphthalenedicarboxylic acid. Nickel-containing hydrogenation catalysts can be used. However, the preferable hydrogenation catalysts are the members of the Group VIII noble metals that include platinum, palladium, rhodium, ruthenium, osmium, iridium and mixtures thereof. Platinum, palladium and ruthenium are particularly effective hydrogenation catalysts for the method of this invention. The aforementioned Group VIII metals can be used in a form supported on a suitable support material, or they can be used in an unsupported form. Although inorganic support materials such as alumina, silica-alumina, silica, clays, zirconia, etc. can be used, supports made from carbon and/or charcoal are substantially inert and are, therefore, highly suitable. The amount of one or more of the aforementioned Group VIII metals on the support; preferably carbon and/or charcoal, is about 0.1 wt. % to about 5.0 wt. %, based on the weight of the catalyst. The amount of catalyst used is a function of, for example, the reaction temperature, concentration of impurities in the naphthalenedicarboxylic acid, and the reaction residence time. However, in general, the weight ratio of impure naphthalenedicarboxylic acid to active component of the hydrogenation catalyst is about 200:1 to about 30,000:1, more preferably 2,000:1 to about 20,000:1. Highly preferred catalysts are 0.03–1.0 wt. % palladium on a high surface area carbon support and 0.03-1.0 wt. % ruthenium on a high surface area carbon support. Such catalysts are available from Engelhard Corp., Edison, N.J.; Degussa Corp, South Plainfield, N.Y.; and Aldrich Chemical Company, Milwaukee, Wis.

The reaction time necessary to achieve acceptable purification of the naphthalenedicarboxylic acid will vary depending on the amount of hydrogenation catalyst used, the concentration of hydrogen and the temperature. However, in general, the reaction residence time or the weight hourly space velocity of the reaction mixture in contact with the hydrogenation catalyst is from about 200 to 200,000 grams of reaction solution per gram of active component of the hydrogenation catalyst, per hour. More preferably, this value is about 1,000 to about 100,000.

After the treatment of the reaction mixture with hydrogen, the reaction mixture is separated from the hydrogenation catalyst. If a continuous process is used wherein the reaction mixture is passed over or through a fixed bed of hydrogenation catalyst, this separation step is not necessary. However, if the hydrogenation catalyst is dispersed in the reaction mixture such as in a batch-type reaction where the hydrogenation catalyst is simply added to the reaction mixture in for example, a granular form, the hydrogenation catalyst must be separated from the reaction mixture by one or more means such as filtration, settling or centrifugation. When the catalyst is used in such dispersed form, it is desirable to use conditions wherein the naphthalenedicarboxylic acid is substantially and, more preferably, completely dissolved in the reaction solvent thereby facilitating the separation of the reaction mixture from the hydrogenation catalyst. However, when operating under reaction conditions wherein all of the naphthalenedicarboxylic acid is not in solution, the hydrogenation catalyst can be contained on one side of a screen or filter or other barrier that permits the passage of dissolved naphthalenedicarboxylic acid, dissolved impurities and hydrogen, but does not permit the passage of undissolved or particulate material such as insoluble impurities and naphthalenedicarboxylic acid not in solution. Using this type of arrangement, the hydrogenation reaction can proceed without subjecting the hydrogenation catalyst to insoluble components that could deactivate the hydrogenation catalyst.

Although not a preferred mode, the purification method of this invention can be conducted by subjecting a hydrogenation catalyst to hydrogen gas in the absence of the impure naphthalenedicarboxylic acid, subsequently using such a hydrogen treated catalyst to treat the impure naphthalenedicarboxylic acid. After the hydrogen absorbed on the catalyst is consumed, the catalyst can once again be exposed to hydrogen gas.

After the reaction mixture is separated from the hydrogenation catalyst the desired, purified naphthalenedicarboxylic acid is recovered from the reaction mixture. Recovery is best accomplished by cooling the reaction mixture to promote the crystallization of dissolved naphthalenedicarboxylic acid. Because the hydrogenation treatment is conducted at an elevated pressure, cooling usually can be achieved by simply reducing the pressure and causing the solution to cool by evaporation of the solvent. This type of cooling can be done so that there is a rapid drop in temperature, i.e. a flash-type of crystallization, or it can be conducted so that there is a gradual drop in temperature by using a series of vessels, each at lower pressure than the previous one. However, any means for cooling the reaction mixture can be used. The degree of cooling, if used, will depend on such variables as the naphthalenedicarboxylic acid present, the amount of solvent used, the temperature used and the desired purity of the naphthalenedicarboxylic acid. In general, however, the reaction mixture is cooled to a temperature in the range of about 100° F. to less than about 500° F. When the reaction mixture is cooled, it is preferable to cool the mixture slowly. Slow cooling facilitates the formation of large particle size naphthalene-dicarboxylic acid. Cooling rates of no more than about 80° F./minute are suitable, more preferably no more than about 50° F./minute. The method of this invention, particularly when the reaction mixture containing purified 2,6-naphthalenedicarboxylic acid is slowly cooled, provides for 2,6-naphthalenedicarboxylic acid having a mean (average) particle size of at least about 100 microns. 2,6-Naphthalenedicarboxylic acid having a mean particle size of at least about 200 microns has also been prepared. Significantly, the 2,6-naphthalenedicarboxylic acid prepared by the method of this invention also has a very small percentage of "fines." For example, less than 15 wt. % of the 2,6-naphthalenedicarboxylic has a particle size below about 11 microns. The mean particle size and the percentage of particles below 11 microns were determined using a Microtrac ® particle size analyzer.

The purified naphthalenedicarboxylic acid is separated from the reaction mixture by any suitable means such as by filtration, centrifugation, settling, and the like. The separated, purified naphthalenedicarboxylic acid is advantageously washed with one or more solvents to remove the last traces of mother liquor adhering to the recovered naphthalenedicarboxylic acid. The solvent used for this washing step is preferably the same solvent used for the hydrogenation step or some other low molecular weight carboxylic acid. However, a different solvent such as water, an aromatic solvent such as toluene, a xylene or other alkyl aromatic solvent, or a halogenated aromatic solvent such as chlorobenzene, can be used. The ratio of wash solvent to naphthalenedicarboxylic acid is suitably about 0.2:1 to about 2:1. The solvent used to wash the recovered naphthalenedicarboxylic acid can be at ambient temperature or even below ambient temperature, however, it is most effective when the solvent used to wash the naphthalenedicarboxylic acid is at an elevated temperature, for example at a temperature of from about 100° F. to about 500° F. Additionally, more than one washing step can be used, either with the same or different solvents.

The mother liquor obtained from the hydrogenation reaction after the naphthalenedicarboxylic acid is separated therefrom can, at least in part, be recycled to the hydrogenation reactions. Alternatively, part or all of the solvent can be first removed by, for example, distillation, and the residue can be at least in part recycled to the oxidation reaction mixture. The mother liquor typically contains valuable residual amounts of naphthalenedicarboxylic acid, intermediates that are oxidized further to naphthalenedicarboxylic acid, and reaction solvent. Similarly, the solvent used to wash the purified naphthalenedicarboxylic acid contains material suitable for recycle to the hydrogenation and/or oxidation reaction steps.

After the naphthalenedicarboxylic acid is separated from the hydrogenation reaction mixture and optionally washed, it is typically dried to remove the last traces of solvent.

Purified solid 2,6-naphthalenedicarboxylic acid that can be prepared by the method of this invention contains very low levels of trimellitic acid, for example, less than about 0.5 wt. %, very low levels of 2-formyl-6-naphthonic acid, for example, less than about 0.1 wt. %; and very low levels of bromo-2,6-naphthalenedicarboxylic acids, for example, less than about 0.05 wt. %. Additionally, it has a large mean particle size of at least about 100 microns, and wherein less than about 2 wt. % of the 2,6-naphthalenedicarboxylic acid has a particle size under 11 microns. 2,6-Naphthalenedicarboxylic acid having a large mean particle size and a low percentage of fine particles such as that prepared by the method of this invention is easily separated from the reaction mixture and is easily washed free of mother liquor because such 2,6-naphthalenedicarboxylic acid does not as readily plug filters, centrifuge screens and other devices used for solid-liquid separation. Additionally, large particle size 2,6-naphthalenedicarboxylic acid can be used to prepare low viscosity slurries with glycols such as ethylene glycol. The slurries are used in processes to prepare PEN and a low viscosity slurry is desirable for such processes, otherwise excessively high amounts of ethylene glycol must be used which tend to form ether impurities during the polymerization process.

A great advantage of the present invention is that the impure naphthalenedicarboxylic acid, particularly 2,6-naphthalenedicarboxylic acid, can be purified without the use of the mono- and/or dialkali salt of the naphthalenedicarboxylic acid, or other derivative such as some other salt, ester or anhydride. The impure naphthalenedicarboxylic acid used in the purification method, as well as the naphthalenedicarboxylic acid present during the purification method of this invention, is preferably mostly in the protonated acid form, i.e. where the carboxylate groups are in the protonated or hydrogen form, and more preferably where at least about 90 mole percent of the naphthalenedicarboxylic acid is in the protonated form, and most preferably wherein substantially all of the naphthalenedicarboxylic acid is in the protonated or hydrogen form, rather than being a salt, ester, anhydride or other derivative. The ability to purify a naphthalenedicarboxylic acid, particularly 2,6-naphthalenedicarboxylic acid, without converting it to some soluble derivative, allows for the direct purification of the naphthalenedicarboxylic acid and, consequently the elimination of process steps wherein the derivative is converted back to the desired naphthalenedicarboxylic acid.

The method of this invention can be conducted in the batch mode wherein the solvent, catalyst and impure naphthalenedicarboxylic acid are added to a suitable reaction vessel and exposed to hydrogen at the hereinabove described reaction conditions. At the end of the reaction, the product mixture is removed from the reactor vessel. In a continuous mode, the impure naphthalenedicarboxylic acid and low molecular weight carboxylic acid are contacted with the hydrogen gas while flowing through a reactor vessel at predetermined flow rates. In such a continuous mode the catalyst is typically contained within the reactor vessel such as, for example, in the form of a fixed bed of catalyst.

The following examples are being provided to illustrate certain embodiments of the invention, however, they are not intended to limit the scope thereof.

In the following Examples and Tables, 2,6-naphthalenedicarboxylic acid is 2,6-NDA, 2,7-naphthalenedicarboxylic acid is 2,7-NDA, trimellitic acid is TMLA, the bromo-2,6-naphthalenedicarboxylic acids are Br-2,6-NDA, 2-formyl-6-naphthoic acid is 2-FNA and 2-naphthoic acid is 2-NA. Organic components were analyzed by liquid chromotography. Metals and bromine were measured using X-ray fluorescence spectroscopy. Values in the Tables reported as 0.00 indicates the component was not detected by the method of analysis used.

Values in the Tables and Examples referred to as "Normalized 2,6-NDA", were obtained by dividing the actual percent 2,6-NDA obtained directly from the liquid chromatographic analysis by the "Total" value reported and multiplying by 100. Because of the magnitude of signal for the 2,6-NDA component, the actual value obtained is a less accurate measurement of concentration. The value was, therefore, normalized as described above.

Particle size was measured using a Microtrac II TM Standard Range Analyzer manufactured by Leeds and Northrop Co., St. Petersburg, Fla. Methanol (or water) was used as the circulating liquid for suspending the 2,6-naphthalenedicarboxylic acid particles. This method is based on laser light scattering, and provides both a mean (average) particle size and a percent distribution which can be used to calculate the weight percentage of particles having a particle size less than 11 microns.

The crude 2,6-naphthalenedicarboxylic acid used for the following Examples was obtained by the liquid phase, air oxidation of 2,6-dimethylnaphthalene in acetic acid/water solvent catalyzed by cobalt II acetate, manganese II acetate and hydrogen bromide as the promoter.

EXAMPLE 1

For Runs 1–8 reported in Table 1, a 50 ml high pressure reactor fitted with an internal thermocouple was charged with the indicated solvents and crude 2,6-NDA having the composition listed in Table 1. A wire mesh basket containing a 0.5% Pd/carbon catalyst in the form of granules was inserted into the reactor. The catalyst was previously heated in the solvent alone for several hours at 540° F. to "age" it and impart more stability to the catalyst. Finally, the reactor was purged with hydrogen gas to remove the oxygen and pressurized with the indicated amount of hydrogen gas and sealed.

The reactor was placed in the shaker device which agitated the reactor contents by shaking at 360 cycles/minute. While shaking, the reactor was partially immersed into a sand bath to attain the desired temperature as measured by the internal thermocouple. The shaking and reaction temperature was maintained for 30 minutes as indicated in Table 1. After the reaction period, the reactor was withdrawn from the sand bath, cooled to room temperature, weighed to determine reactor integrity, and the entire reactor contents transferred to a dish for drying in a vacuum oven at 175°–195° F.

The dry total product was mixed well for uniformity of sampling and analyzed by liquid chromatography. The product contained the 8-carbon diacids (C$_8$ acids): terephthalic (TA), isophthalic (IA), and phthalic acid (OA). As noted, the product also contained trimellitic acid, 2-naphthoic acid, 2-methyl-6-naphthoic acid, and the ring hydrogenated product, 2,6-dicarboxytetralin.

Runs 1-3 were conducted with 85% acetic acid and 15% water using various hydrogen pressures. In all cases all of the Br-2,6-NDA was converted, 62-72% of the TMLA, and 61-71% of the 2-FNA. The amount of 2-NA formed by decarboxylation of 2,6-NDA ranged from 0.0 to 0.06 wt. %. The amount of dicarboxytetralin increased with increasing hydrogen pressure and ranged from 0.02 to 0.14%. Thus, high conversion of impurities was obtained along with low formation of by-products.

In Runs 4-6, a 50/50 mixture of acetic acid/water was used. The conversion of Br-2,6-NDA was 100% just as with the 85% acetic acid. The conversion of TMLA and 2-FNA was somewhat higher than with the 85% acetic acid. The amount of 2-NA and the amount of tetralin formed was greater than with the 85% acetic acid.

In Runs 7-8, pure water was used as the solvent to compare with the acetic acid cases. While the TMLA conversion was as much as 30% higher than with the acetic acid/water cases, the amount of 2-FNA conversion was comparable but the amount of 2-NA formation was three times higher than with 85% acetic acid and about twice as high as with 50% acetic acid. The formation of the tetralin was also one to three times higher than with 85% acetic acid.

EXAMPLE 2

In Runs 1-2 reported in Table 2, two comparison runs were made in a large stirred high pressure reactor which was charged with the identical 2,6-NDA starting material, hydrogen gas pressure, and catalyst for both runs. In Run 1, the solvent was water and in Run 2 the solvent was 90 wt. % acetic acid/10 wt. % water. Both runs were made at similar conditions except that twice the reaction time was used for Run 2 to obtain higher conversion of 2-FNA and to test the formation of undesirable by-products. One advantage of using acetic acid rather than pure water solvent is that the acetic acid vapor pressure is lower allowing operation at 500 psig lower pressure at 590° F. Following the reaction period, both runs were cooled to 300° F. and filtered through a screen in the bottom of the reactor. The cake was then washed in the reactor at 300° F. with an additional 400 g of the same solvent used in the original charge and the mother liquor removed by filtration was added to the first mother liquor.

The mother liquor and cake were both dried in a vacuum oven at 175°-195° F., individually mixed for uniformity and each was analyzed by liquid chromatography for organic composition and by x-ray fluorescence spectroscopy for metals. The cake samples were analyzed by a Microtrac TM particle size analyzer for particle size. The weights and compositions of the filtrate and cake were used to calculate the total product composition which is reported in Table 2 as the "Combined Products."

Comparison of the "Combined Products" in Table 2 indicates that the 2-FNA and the TMLA conversion was higher for Run 2 (90% acetic acid) than for Run 1. This can be explained by the longer reaction period for this Example 2. However, it is most important to notice that in spite of the longer reaction period, the formation of the 2-NA was lower for Run 2.

The metal content of the two cakes differed significantly. Using water as solvent, there was about three times as much metal remaining in the cake compared to using 90% acetic acid. The particle size produced from either solvent was significantly larger than for the feed allowing ready recovery of the solid from the slurry.

EXAMPLE 3

Solubility data for 2,6-naphthalenedicarboxylic acid in distilled water and in acetic acid are provided below:

| Temperature | Solubility (gram 2.6-NDA/100 g solvent) | | |
|---|---|---|---|
| | Water | Acetic Acid | Acetic Acid/Water* |
| 160/320 | 0.041 | 0.16 | 0.18 |
| 200/342 | 0.22 | 0.44 | 0.59 |
| 240/464 | 1.19 | 1.2 | 2.0 |
| 280/536 | 6.07 | 3.1 | 4.5 |
| 320/608 | 33.2 | — | 10.8 |

*85 wt. % acetic acid and 15 wt. % water.

TABLE 1

| Run # | 2,6-NDA Feed[a] | 1 | 2 | 3 | 4 | 5 | 6 | 7 | 8 |
|---|---|---|---|---|---|---|---|---|---|
| Reactor Charge | | | | | | | | | |
| 2,6-NDA (g) | | 4.00 | 4.01 | 4.00 | 4.00 | 4.00 | 4.00 | 4.00 | 4.00 |
| Solvent Used (Wt. % Acetic Acid/Wt. % Water) | | 85/15 | 85/15 | 85/15 | 50/50 | 50/50 | 50/50 | 0/100 | 0/100 |
| Solvent Wt. (g) | | 20.0 | 20.0 | 20.0 | 20.0 | 20.0 | 20.0 | 20.0 | 20.0 |
| Catalyst Used[b] | | 0.5 wt. % Pd/c | 0.5 wt. % Pd/c | 0.5 wt. % Pd/c | 0.5 wt. % Pd/c | 0.5 wt. % Pd/c | 0.5 wt. % Pd/c | 0.5 wt. % Pd/c | 0.5 wt. % Pd/c |
| Catalyst Wt. (g) | | 0.43 | 0.43 | 0.43 | 0.42 | 0.42 | 0.42 | 0.42 | 0.42 |
| Catalyst Prevous Used | | 2 | 0 | 1 | 2 | 0 | 1 | 4 | 3 |
| Conditions | | | | | | | | | |
| Temperature (°F.) | | 600 | 600 | 600 | 600 | 600 | 600 | 600 | 600 |
| Time from 100° F. to Reaction Temp. (min.) | | 2:05 | 2:10 | 2:30 | 1:50 | 1:50 | 2:00 | 1:50 | 1:45 |
| Reaction Time (min.) | | 30 | 30 | 30 | 30 | 30 | 30 | 30 | 30 |
| Shaking Speed (cpm) | | 360 | 360 | 360 | 360 | 360 | 360 | 360 | 360 |
| Hydrogen Pressure at 70° F. (psig) | | 15 | 30 | 100 | 15 | 30 | 100 | 15 | 100 |
| Product Weight (g)[c] | | 24.20 | 24.29 | 24.26 | 23.96 | 24.17 | 24.19 | 23.90 | 24.02 |
| Wt. % Reactor Loss (g) | | 3.20 | 2.84 | 2.96 | 4.16 | 3.32 | 3.24 | 4.40 | 3.92 |
| Dry Down Weight (g) | | 3.98 | 3.94 | 3.95 | 4.00 | 3.99 | 3.93 | 3.92 | 3.87 |
| Product Analysis (Wt. %) | | | | | | | | | |
| 2,6-NDA | 90.06 | 91.98 | 88.01 | 89.21 | 92.64 | 89.24 | 89.45 | 93.11 | 92.19 |
| 2,7-NDA | 0.01 | 0.00 | 0.01 | 0.01 | 0.00 | 0.01 | 0.01 | 0.00 | 0.00 |
| TMLA | 2.19 | 0.60 | 0.70 | 0.82 | 0.15 | 0.33 | 0.60 | 0.07 | 0.15 |
| C$_8$ Acids | 0.02 | 1.15 | 0.98 | 0.79 | 1.35 | 1.31 | 1.16 | 1.56 | 1.47 |

TABLE 1-continued

| Run # | 2,6-NDA Feed[a] | 1 | 2 | 3 | 4 | 5 | 6 | 7 | 8 |
|---|---|---|---|---|---|---|---|---|---|
| Br-2,6-NDA | 0.59 | 0.00 | 0.00 | 0.00 | 0.00 | 0.00 | 0.00 | 0.00 | 0.00 |
| 2-FNA | 0.30 | 0.10 | 0.08 | 0.12 | 0.08 | 0.04 | 0.08 | 0.11 | 0.07 |
| 2,6-Methyl-NA[d] | 0.01 | 0.06 | 0.07 | 0.07 | 0.06 | 0.07 | 0.08 | 0.06 | 0.07 |
| 2-NA | 0.00 | 0.00 | 0.06 | 0.06 | 0.00 | 0.10 | 0.10 | 0.18 | 0.18 |
| Dicarboxytetralin | 0.00 | 0.02 | 0.05 | 0.14 | 0.05 | 0.16 | 0.36 | 0.05 | 0.23 |
| Others | 0.39 | 0.42 | 0.25 | 0.31 | 0.35 | 0.17 | 0.21 | 0.24 | 0.23 |
| Total | 93.55 | 94.32 | 90.23 | 91.52 | 94.68 | 91.43 | 92.05 | 95.37 | 94.59 |
| Normalized 2,6-NDA | 96.3 | 97.5 | 97.5 | 97.5 | 97.8 | 97.6 | 97.2 | 97.6 | 97.5 |
| Weight % Conversion | | | | | | | | | |
| TMLA | | 72.5 | 67.9 | 62.4 | 93.0 | 84.9 | 72.5 | 97.0 | 93.0 |
| Br-2,6-NDA | | 100.0 | 100.0 | 100.0 | 100.0 | 100.0 | 100.0 | 100.0 | 100.0 |
| 2-FNA | | 67.5 | 71.5 | 61.0 | 71.9 | 86.5 | 72.4 | 62.4 | 77.6 |

[a]Contained (Wt. %): Cobalt (0.125), manganese (0.75), bromine (0.373). Particle size of 20.9 (mean) and 24% less than 22 microns.
[b]0.5 Weight percent palladium on carbon support
[c]Weight of total reactor effluent
[d]2-Methyl-6-naphthoic acid

TABLE 2

| Run # | 1 | 2 |
|---|---|---|
| Reactor Charge | | |
| 2,6-NDA[a] (g) | 200 | 200 |
| Solvent Used (wt. % Acetic acid/wt. % water) | (0/100) | (90/10) |
| Solvent Wt. (g) | 1000 | 1005 |
| Catalyst Used[b] | 0.5 Wt. % Pd/C | 0.5 Wt. % Pd/C |
| Catalyst Wt. (g) | 4.5 | 4.5 |
| Catalyst Prior Uses | 0 | 0 |
| Conditions | | |
| Temperature (°F.) | 590 | 595 |
| Pressure (psig) | 1480 | 970 |
| Reaction Time (min) | 60 | 120 |
| Hydrogen Pressure at Room Temp. (psig) | 50 | 50 |

| | 1A Cake | 1B Filtrate | 1C Combined Products | 2A Cake | 2B Filtrate | 2C Combined Products |
|---|---|---|---|---|---|---|
| % of Total | 94.80 | 5.20 | | 88.80 | 11.20 | |
| Product Analysis (wt. %) | | | | | | |
| 2,6-NDA | 93.27 | 16.60 | 89.30 | 94.54 | 22.49 | 86.47 |
| 2,7-NDA | 0.00 | 0.36 | 0.02 | 0.00 | 0.16 | 0.02 |
| TMLA | 0.00 | 2.46 | 0.13 | 0.00 | 0.27 | 0.03 |
| Br-2,6-NDA | 0.00 | 0.06 | 0.00 | 0.03 | 0.03 | 0.03 |
| 2-FNA | 0.09 | 0.97 | 0.13 | 0.01 | 0.19 | 0.03 |
| 2-NA | 0.00 | 7.22 | 0.37 | 0.00 | 1.74 | 0.20 |
| Others | 0.32 | 56.28 | 3.22 | 0.37 | 25.75 | 3.21 |
| Total | 93.68 | 83.96 | 93.17 | 94.95 | 50.63 | 89.98 |
| Normalized %, 2,6-NDA | 99.6 | 19.8 | 95.84 | 99.57 | 44.42 | 96.10 |
| Metal Analysis (wt. %) | | | | | | |
| Cobalt | 0.03 | 1.38 | 0.10 | 0.01 | 0.80 | 0.10 |
| Manganese | 0.29 | 6.40 | 0.60 | 0.08 | 5.50 | 0.69 |
| Bromine | 0.01 | 8.00 | 0.42 | 0.03 | 2.82 | 0.34 |
| Wt. % Conversions | | | | | | |
| TMLA | | | 94.2 | | | 98.6 |
| Br-2,6-NDA | | | 99.5 | | | 95.2 |
| 2-FNA | | | 54.9 | | | 88.5 |
| % Loss of Bromine | | | −12.7 | | | 8.1 |
| Particle Size | | | | | | |
| Mean (microns) | 358 | | | 179 | | |
| % < 11 microns | 0 | | | 0.3 | | |

[a]Same 2,6-NDA feed as reported on Table 1, Particle Size 20.9 microns (mean) and 24% < 11 microns.
[b]Catalyst was aged by heating at 530° F. for 72 hours in a 20 wt. %/80 wt. % terephthalic acid/water mixture.

Only certain embodiments of the invention have been set forth and alternative embodiments and various modifications will be apparent from the above description to those skilled in the art. These and other alternatives are considered equivalents and within the spirit and scope of the present invention.

That which is claimed is:

1. A method for purifying a naphthalenedicarboxylic acid comprising a) contacting a naphthalenedicarboxylic acid with hydrogen in the presence of a hydrogenation catalyst and a solvent comprising a low molecular weight carboxylic acid, at a temperature of at least about 500° F., and a pressure sufficient to maintain the solvent at least partially in the liquid phase, and thereafter b) recovering purified naphthalenedicarboxylic acid.

2. The method of claim 1 wherein the naphthalenedicarboxylic acid is 2,6-naphthalenedicarboxylic acid.

3. The method of claim 1 wherein the temperature is at least about 600° F. and no more than about 700° F.

4. The method of claim 2 wherein the 2,6-naphthalenedicarboxylic acid is prepared by the liquid phase oxidation of 2,6-dimethylnaphthalene, in an oxidation reaction mixture comprising molecular oxygen, a solvent comprising an aliphatic $C_2$–$C_6$ monocarboxylic acid, and a catalyst comprising cobalt, manganese and bromine components.

5. The method of claim 1 wherein the solvent comprises acetic acid.

6. The method of claim 1 wherein the solvent comprises a mixture of water and acetic acid, wherein the water is present in an amount of about 15 weight percent to about 85 weight percent of the solvent.

7. The method of claim 1 wherein the hydrogenation catalyst comprises at least one Group VIII noble metal.

8. The method of claim 7 wherein the Group VIII noble metal is platinum, palladium or ruthenium.

9. The method of claim 3 wherein the naphthalenedicarboxylic acid is contacted with the solvent comprising a low molecular weight carboxylic acid and the naphthalenedicarboxylic acid is substantially in solution.

10. The method of claim 1 wherein in step b) the recovery comprises cooling the reaction mixture resulting from step a) to a temperature below about 500° F. and thereafter separating solid naphthalenedicarboxylic acid from the cooled mixture.

11. The method of claim 10 wherein the reaction mixture is cooled at a rate of no more than about 80° F./minutes.

12. The method of claim 2 wherein the recovered 2,6-naphthalenedicarboxylic acid has a mean particle size of at least about 100 microns.

13. The method of claim 2 wherein the recovered 2,6-naphthalenedicarboxylic acid has a mean particle size of at least about 200 microns and wherein less than about 15 weight percent of the particles have a particle size less than 11 microns.

14. The method of claim 1 conducted in the batch mode.

15. The method of claim 1 conducted in the continuous mode.

16. The method of claim 1 wherein the solvent comprises a saturated low molecular weight monocarboxylic acid containing 2 to about 6 carbon atoms.

17. The method of claim 16 wherein the solvent contains about 5 to about 95 weight percent water.

18. The method of claim 1 wherein the naphthalenedicarboxylic acid in steps a) and b) is at least 90 mole percent in the protonated form.

19. A method for purifying 2,6-naphthalenedicarboxylic acid comprising a) contacting impure 2,6-naphthalenedicarboxylic acid hydrogen in the presence of a Group VIII noble metal hydrogenation catalyst and a solvent comprising acetic acid, at a temperature of about 600° F. to about 700° F., and at a pressure sufficient to maintain the solvent at least partially in the liquid phase, b) cooling the reaction mixture formed by step a) to a temperature below about 500° F. and, thereafter c) separating solid 2,6-naphthalenedicarboxylic acid from the cooled reaction mixture.

20. The method of claim 19 wherein the Group VIII metal is selected from the group consisting of platinum, palladium and ruthenium.

21. The method of claim 19 wherein the impure 2,6-naphthalenedicarboxylic acid is prepared by the liquid phase oxidation of 2,6-dimethylnaphthalene, in the presence of a catalyst comprising cobalt, manganese and bromine components, a molecular oxygen-containing gas, and a solvent comprising acetic acid.

22. The method of claim 19 wherein the 2,6-naphthalenedicarboxylic acid is at least 90 mole percent in the protonated form.

* * * * *

UNITED STATES PATENT AND TRADEMARK OFFICE
CERTIFICATE OF CORRECTION

PATENT NO. : 5,256,817
DATED : October 26, 1993
INVENTOR(S) : David L. Sikkenga, Stephen V. Hoover It is certified that error appears in the above-indentified patent and that said Letters Patent is hereby corrected as shown below:

| Col. | Line | |
|---|---|---|
| 11 | 7 | "naphthonic acid," should read --naphthoic acid,-- |
| 15 | 15 | in Table 1, in the footnote labeled "a," patent reads "22 microns" should read--11 microns-- |

Signed and Sealed this

Sixteenth Day of August, 1994

Attest:

BRUCE LEHMAN

Attesting Officer     Commissioner of Patents and Trademarks